(12) United States Patent
Degelmann et al.

(10) Patent No.: US 6,414,138 B1
(45) Date of Patent: *Jul. 2, 2002

(54) PROCESS FOR PRODUCING MIXTURES RICH IN 1,6-GPS OR 1,1-GPM

(75) Inventors: Hanspeter Degelmann; Michael Gander, both of Worms; Jörg Kowalczyk, Bockenheim; Markwart Kunz, Worms; Mohammad Munir, Kindenheim; Matthias Schüttenhelm; Wolfgang Wach, both of Worms, all of (DE)

(73) Assignee: Sudzucker Aktiengesellschaft, Mannheim (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/018,359

(22) Filed: Feb. 4, 1998

(30) Foreign Application Priority Data

Feb. 14, 1997 (DE) .......................... 197 05 664

(51) Int. Cl.[7] ..................... C07H 1/00; C08B 37/00

(52) U.S. Cl. ............... 536/124; 536/123.1; 536/123.13; 536/127

(58) Field of Search ........................ 536/124, 123.13, 536/127, 123.1

(56) References Cited

U.S. PATENT DOCUMENTS

| 3,865,957 A | 2/1975 | Schieweck et al. | 426/213 |
|---|---|---|---|
| 4,117,173 A | 9/1978 | Schiweck et al. | 426/548 |
| 4,233,439 A | 11/1980 | Schiweck et al. | 536/4 |

OTHER PUBLICATIONS

Strater, Palatinit–Technological and Processing Characteristics, Alternative Sweetners, pp. 217–244, 1986.*

* cited by examiner

*Primary Examiner*—James O. Wilson
*Assistant Examiner*—Howard V Owens, Jr.
(74) *Attorney, Agent, or Firm*—Darby & Darby

(57) ABSTRACT

The invention relates to a process for producing mixtures selectively enriched with either 1,1-GPM and 1,6-GPS from hydrogenated isomaltulose. The process involves dissolving hydrogenated isomaltulose at an elevated temperature, and subjecting the resulting solution to one or more cooling steps, wherein each cooling step utilizes a predetermined cooling rate over a predetermined temperature range.

24 Claims, 4 Drawing Sheets

PROCESS FOR PRODUCING MIXTURES RICH IN 1,6-GPS OR 1,1-GPM

BACKGROUND OF THE INVENTION

The present invention relates to a process for producing mixtures enriched with 6-0-α-D-Glucopyranosyl-D-sorbite (hereinafter, 1,6-GPS) and/or 1-0-α-D-Glucopyranosyl-D-mannite (hereinafter, 1,1-GPM) from hydrogenated isomaltulose or from mixtures containing hydrogenated isomaltulose.

Hydrogenated isomaltulose is an almost equimolar mixture of 1,6-GPS and 1,1-GPM and is a commercially available sugar substitute. Its acariogenicity, low calorie content, and suitability for diabetics provide substantial benefits. Pure 1,6-GPS and 1,1-GPM or mixtures containing larger amounts of 1,6-GPS and 1,1-GPM can be advantageously used in a number of applications, such as, for example, in the food industry, where these solutions are superior to products containing equimolar ratios of 1,1-GPM/1,6-GPS. However, manufacturing processes for producing mixtures enriched with 1,6-GPS or 1,1-GPM or pure 1,6-GPS and 1,1-GPM which enable a simple and efficient production from a readily available starting material, are not known to date.

SUMMARY OF THE INVENTION

It is therefore an object of the invention to provide a suitable manufacturing process for producing large quantities of pure 1,1-GPM and 1,6-GPS as well as mixtures of 1,1-GPM. and 1,6-GPS with a high yield.

The object is achieved by the process for producing mixtures enriched with 1,1-GPM and 1,6-GPS as well as pure 1,6-GPS and pure 1,1-GPM, which comprises:

(i) dissolving hydrogenated isomaltulose or a mixture containing hydrogenated isomaltulose in water at an elevated temperature;

(ii) subjecting the solution produced in step (i) to one or more cooling steps to produce distinct phases enriched in 1,1-GPM or 1,6-GPS, wherein each cooling step comprises cooling the solution at a predetermined rate over a predetermined temperature range; and (iii) separating the phase enriched with 1,1-GPM from the phase enriched with 1,6-GPS.

The phases enriched with 1,1-GPM or 1,6-GPS are produced with the process of the invention by dissolving hydrogenated isomaltulose or a mixture containing hydrogenated isomaltulose in water at elevated temperatures and cooling the solution over a predetermined temperature range to crystallize the solution and to obtain the desired phase composition. The 1,1-GPM-rich phase is subsequently separated from the 1,6-GPS-rich phase, preferably by centrifugation. The cooling process for the crystallization can be either discontinuous or continuous.

In a preferred embodiment, the solution is cooled to crystallize in a temperature range from about 90° C. to about 65° C. at a cooling rate of 5 to 15 K/h and in a temperature range from about 75° C. to 37° C., in particular 65° C. to 37° C., at a cooling rate of 0.4 to 10 K/h, preferably of 0.4 to 3 K/h.

In the context of the present invention, hydrogenated isomaltulose is defined as an equimolar or almost equimolar mixture of 1,1-GPM and 1,6-GPS. A mixture containing hydrogenated isomaltulose is defined as a mixture of 1,1-GPM, 1,6-GPS as well as of one or more substances, including without limitation mannite, sorbite, saccharose, 1,1-GPS (1-0-α-D-Glucopyranosyl-D-sorbite), isomaltose, hydrogenated or unhydrogenated oligosaccharides, isomelezitose, or other substances. Suitable starting materials for the process of the invention are, for example, the sweeteners described in EP 0 625 578 B1.

Within the framework of the present invention, a temperature is defined as elevated if the hydrogenated isomaltulose or the mixture containing the hydrogenated isomaltulose can be completely or almost completely dissolved in water, provided that the prescribed starting concentration is used in the cooling crystallization, for example 70 to 90 wt. % solid phase content.

DESCRIPTION OF THE PREFERRED EMBODIMENTS

Figure 1:
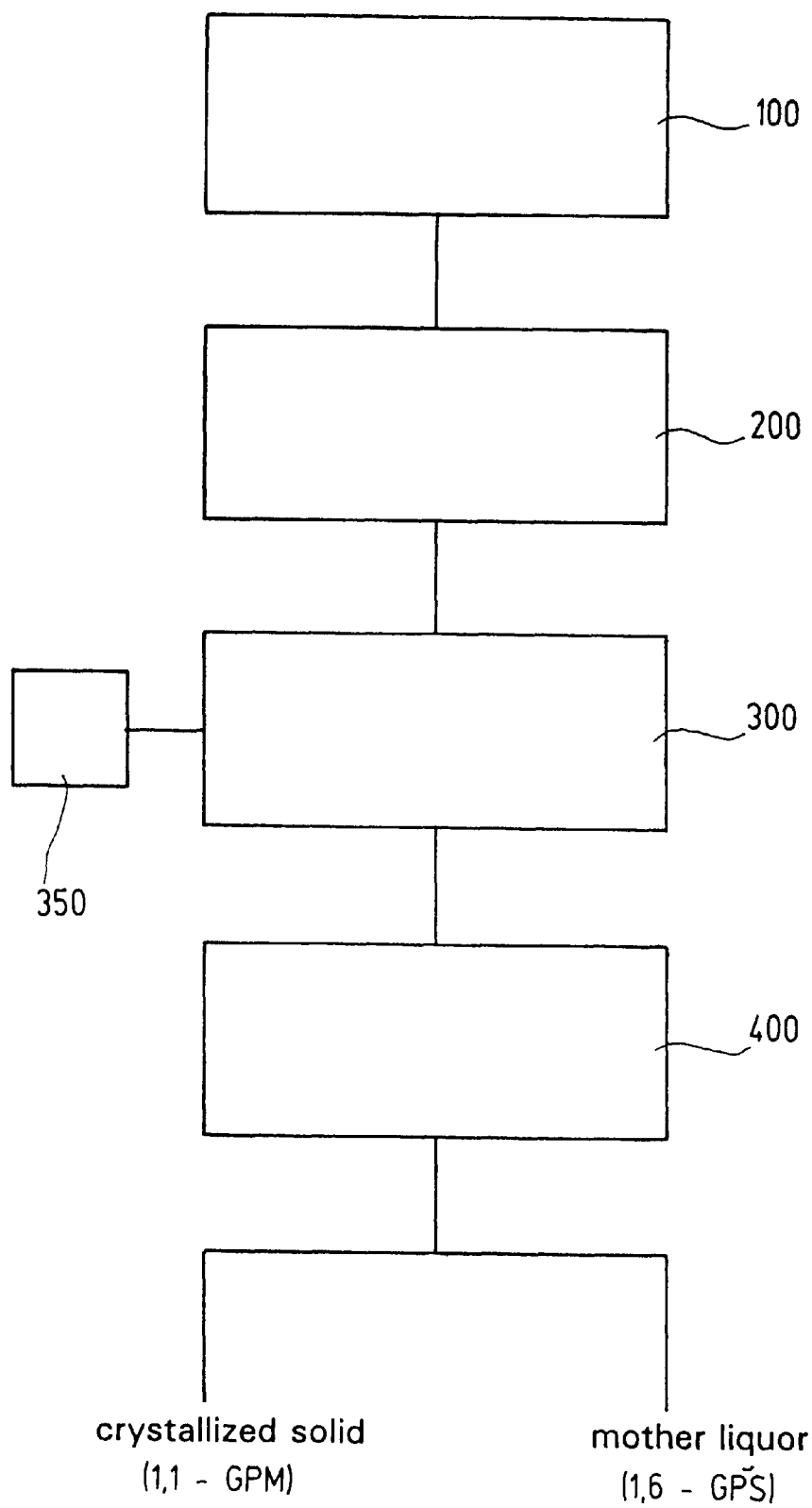
FIG. 1 is a schematic illustration of the process for producing phases enriched with 1,1-GPM and 1,6-GPS.

The invention is based on the observation that 1,1-GPM and 1,6-GPS have different solubilities in water and that the two components reach their respective solubility equilibrium very quickly, for example in less than half an hour. Since the solubility equilibrium is temperature-dependent, the concentration ratio of the two components can advantageously be preset. After the solubility equilibrium is adjusted, the 1,1-GPM and 1,6-GPS concentration in the products can be controlled by setting the rate for the temperature change.

In a preferred embodiment of the invention, a cooling rate of 5 to 15 K/h is advantageously maintained in a temperature range between about 90° C. and about 65° C., and a cooling rate of 0.4 to 10 K/h, preferably of 0.4 to 3 K/h, is maintained in a temperature range between about 65° C. and about 37° C.

The indicated ranges do not imply that the substances must be cooled over the entire specified temperature range to crystallize or that this temperature range may not be exceeded. These values only imply that the specified cooling rate has to be maintained if the substances cooled are to crystallize within the specified temperature range.

The initial and final temperatures for crystallization by cooling, i.e. the prescribed temperature interval, also depend on the concentration and the composition of the starting material and on the purity desired for the product and can be determined through routine experimentation. The temperature interval selected for crystallization by cooling should also yield sufficiently large crystals so that these crystals can be efficiently separated. The resulting phases should also be sufficiently concentrated with respect to 1,1-GPM and 1,6-GPS, respectively, for example, contain more than 70 wt. % solid phase content, preferably more than 80 wt. % solid phase content, and most preferably more than 85 wt. % solid phase content of 1,1-GPM and 1,6-GPS, respectively. Most advantageously, crystallization by cooling begins at a temperature of about 80–90° C., preferably at about 85° C., and ends at a temperature of about 30–40° C., most preferably at 37° C.

The invention also provides a particularly simple and efficient process for producing pure 1,1-GPM and pure 1,6-GPS or an enriched mixture of these substances, i.e. more than 50 wt. % solid phase content, by taking advantage of the different, but excellent, solubilities of 1,1-GPM and 1,6-GPS, respectively. Advantageously, the grain size of crystallized solids obtained by cooling according to the invention is rather coarse so that the crystals subsequently can be easily separated. The grain size distribution of the resulting 1,1-GPM-rich product is particularly uniform due to the advantageous cooling rate employed in the process of the invention, which is about 5 to about 15 K/h in the temperature range between about 90° C. and about 65° C., and about 0.4 to about 10 K/h, preferably about 0.4 to about 3 K/h, in the temperature range from 75° C. to 37° C., preferably between about 65° C. and about 37° C. Consequently, the product can be readily separated by centrifugation. The 1,1-GPM-rich crystals cannot be separated by centrifugation, if the process conditions of the invention, in particular the cooling rates, are not followed, due to the exceedingly heterogeneous distribution of the grain sizes. Moreover, the average grain size of the resulting crystals becomes too small, so that centrifugation is inefficient. The mother liquor can be separated fast and efficiently from the crystallized solids by centrifugation after the solution is crystallized by cooling, making the process described above very efficient.

In a preferred embodiment, a suspension of hydrogenated isomaltulose or of a mixture containing hydrogenated isomaltulose is initially prepared in water. The suspension is then dissolved by increasing the temperature, whereafter the resulting solution is crystallized by cooling.

In another preferred embodiment, the starting material is a solution which is already enriched with the desired 1,6-GPS or 1,1-GPM components. The solution is then concentrated, for example by evaporation, and subsequently crystallized by cooling.

In yet another preferred embodiment, the starting material is hydrogenated isomaltulose or a crystalline form of one of the sweeteners described in EP 0 625 578 B1 which is dissolved in water at a temperature between about 80–90° C., preferably at about 85° C. The resulting solution contains preferably between about 70 and about 90 wt. % dry solid, most preferably between 75–85 wt. % dry solid.

In still another preferred embodiment, the solution is cooled to crystallize in a temperature range between about 90° C. and about 65° C. at a cooling rate of about 8 to about 12 K/h. In another preferred embodiment, the solution is cooled to crystallize in a temperature range between about 75° C. and about 37° C., preferably between about 65° C. and about 37° C., at a constant cooling rate of about 0.8 to about 1.5 K/h.

In another preferred embodiment of the invention, a suspension which is formed by the addition of, for example, crystalline hydrogenated isomaltulose in water, is heated to, for example, 85° C. to completely dissolve the solute, whereafter the cooling step to crystallize the solution is combined with a seeding step. The seeding step, however, is not essential. Advantageously, powdered hydrogenated isomaltulose in crystalline form or in the form of a suspension can be used. Most advantageously, the suspension is formed in water or in an organic solvent, such as isopropanol, and a food-compatible dispersing agent acting as a solvent can be added, if necessary. A starting material for the suspension can also be pure 1,1-GPM or 1,6-GPS instead of hydrogenated isomaltulose, depending on the desired product. The seeding may be performed, e.g., when the temperature of the solution is between about 50° C. and about 65° C., preferably 61–63° C. After the seed suspension is mixed into the concentrated solution made from, for example, hydrogenated isomaltulose, the readily soluble 1,6-GPS crystals are completely dissolved, whereas the only slightly soluble 1,1-GPM crystals remain as nuclei. It was observed that the resulting 1,1-GPM-rich crystals are particularly large, so that during subsequent centrifugation, the solid matter could be easily separated from the crystal mush. The slight cloudiness of the centrifuge effluent can be eliminated through subsequent pressure filtration.

In still another embodiment, following the crystallization by cooling, the resulting 1,1-GPM-rich phase, i.e. the crystallized solid, is separated from the aqueous 1,6-GPS-rich phase by centrifugation filtration or sedimentation, which advantageously separates the mother liquor from the crystallized solid. The crystallized solid is 1,1-GPM-rich, whereas the mother liquor is 1,6-GPS-rich. The crystallized 1,1-GPM-rich solid already has a purity in excess of 75% solid phase content and can be purified and concentrated further to form pure crystalline 1,1-GPM with a purity greater than 99% solid phase content. The 1,6-GPS-rich mother liquor already has a purity in excess of 80% solid phase content and can be purified and concentrated further to form pure crystalline 1,6-GPS with a purity greater than 99% solid phase content.

Pure 1,1-GPM is produced with the process of the invention from the crystallized 1,1-GPM-rich solid by first dissolving the crystallized solid in water, for example at a temperature between about 55° C. and about 65° C., preferably 60° C., and by subsequently filtering and concentrating the dissolved solid in vacuum, for example at about 85–90° C., preferably at 88° C., if necessary. In a first step, the concentrated solution can be cooled to crystallize in a temperature range between about 75–90° C., preferably 88° C., at a constant cooling rate of about 9 K/h, and in a temperature range between about 75° C. and about 37° C. at a constant cooling rate of about 1 K/h. After the first crystallization by cooling, the resulting substance is centrifuged to separate out a 1,6-GPS-rich mother liquor. The 1,1-GPM content of the resulting crystallized solid is already close to 95 wt. % solid phase content; the crystallized solid is then dissolved in water, preferably at about 90–100° C., more preferably at 95° C. The solution is then cooled for a second time at temperatures between about 95° C. to 65° C., with a cooling rate of about 3 K/h, and at temperatures between about 75° C. and about 40° C., preferably between 65° C. and 40° C., with a cooling rate of about 1 K/h to crystallize the solution. If necessary, the resulting substance is again centrifuged, yielding a 1,1-GPM-rich mother liquor and a 1,1-GPM-rich crystallized solid with a purity of 99 wt. % solid phase content of 1,1-GPM.

Pure 1,6-GPS can be produced from the mother liquor which was obtained when the 1,6-GPS-rich phase was separated from the 1,1-GPM-rich phase by cooling. The 1,6-GPS-rich mother liquor is first concentrated, for example at a temperature between about 50–60° C., preferably at 55° C., and then crystallized by cooling. The preferred cooling rate is about 0.3 K/h over a temperature range between about 60° C., preferably 55° C., and 40° C. If necessary, the concentration step and the crystallization step by cooling are repeated under the same conditions, until a sufficient quantity of crystals with suitable diameters is obtained. The subsequent centrifugation yields a 1,6-GPS-rich mother liquor and a 1,6-GPS-rich crystallized solid with a purity of 99 wt. % solid phase content of 1,6-GPS.

Although specific temperature ranges were specified above for the cooling rates in order to obtain pure 1,1-GPM and 1,6-GPS with the process of the invention, this does not imply that the process operates over the entire specified temperature range or that the process does not exceed this temperature range. The initial and final temperatures, i.e. the given temperature interval or range, for the crystallization process by cooling depend on the type and the concentration of the educts and on the composition desired for the product (degree of crystallization, diameter of the crystals, purity, etc.). For producing 1,1-GPM, a first crystallization is preferably carried out in a temperature interval between about 88° C. and about 37° C. and a second crystallization between about 95° C. and, about 40° C.; the preferred temperature interval for producing 1,6-GPS is between about 55° C. and 40° C.

In yet another embodiment of the invention, the resulting 1,1-GPM-rich and 1,6-GPS-rich products, or pure 1,1-GPM and 1,6-GPS, respectively, can be dried to improve shelf life. According to the invention, moist 1,6-GPS is dried for 5 hours at about 40–50° C., preferably at 45° C. 1,1-GPM is preferably dried for six hours, starting at a drying temperature of, for example, about 35° C. at a constant heating rate of about 1 K/h.

In another embodiment of the invention, the solutions enriched with 1,1-GPM and 1,6-GPS, respectively, or the pure 1,1-GPM and 1,6-GPS, respectively, can be concentrated to about 60–90% solid phase content. The dry, ready-to-use product can subsequently be isolated through a vapor crystallization either with or without a vacuum. This process is easier to carry out if an already dry end product is available.

Additional preferred embodiments of the invention can be found in the dependent claims.

Other objects and features of the present invention will become apparent from the following detailed description considered in conjunction with the accompanying drawings. It is to be understood, however, that the drawings are intended solely for purposes of illustration and not as a definition of the limits of the invention, for which reference should be made to the appended claims.

EXAMPLES

Example 1

Figure 4:
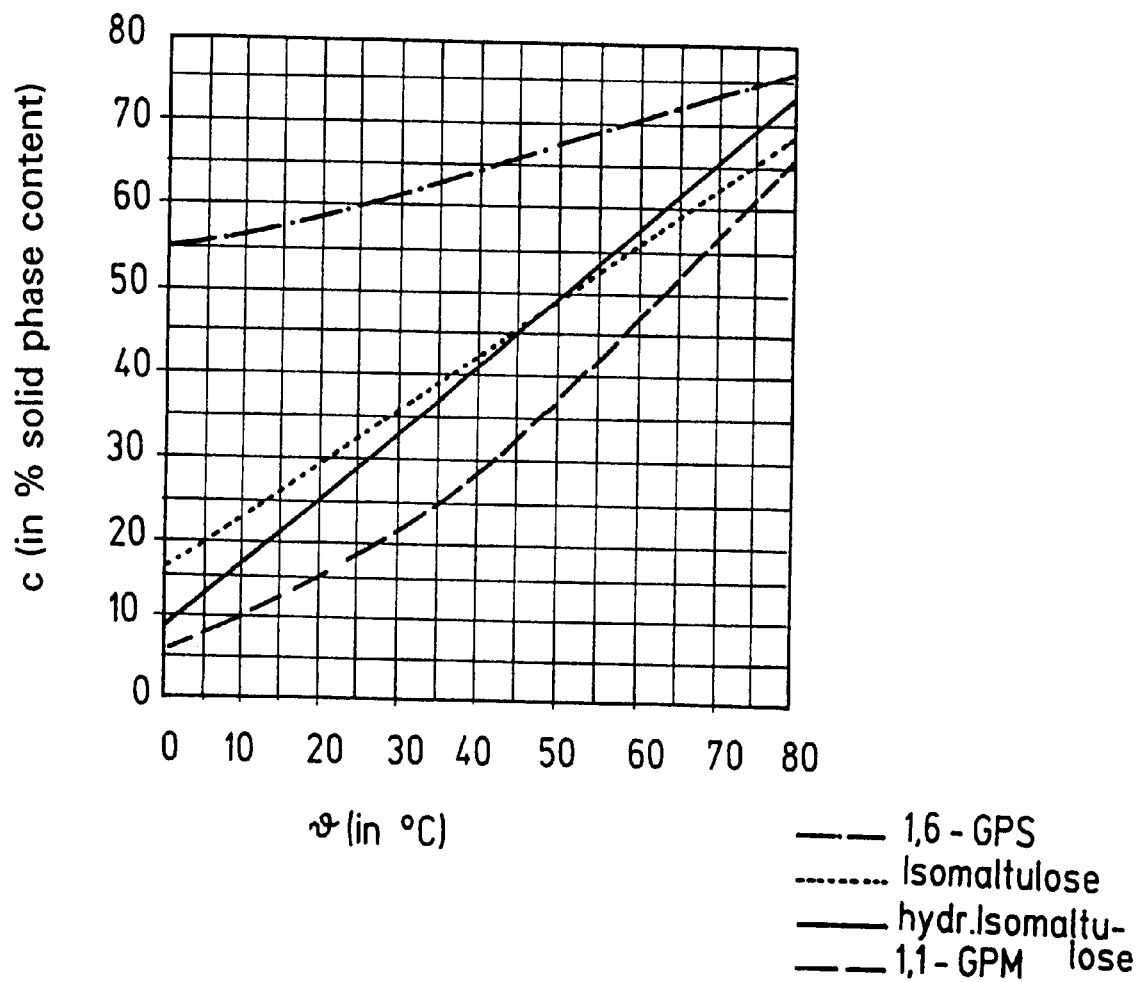
FIG. 4 is a solubility diagram for hydrogenated isomaltulose, isomaltulose, 1,1-GPM and 1,6-GPS.

Separation of Hydrogenated Isomaltulose into 1.1-GPM-rich and 1,6-GPS-rich Phases Through Crystallization by Cooling The two constituents of hydrogenated isomaltulose, i.e. 1,1-GPM and 1,6-GPS, have a different solubility in aqueous solutions (FIG. 4). In suspension, each component reaches its own solubility equilibrium. The 1,1-GPM component, which crystallizes more readily, is concentrated in the solid fraction of the suspension, whereas the 1,6-GPS component, which crystallizes less readily, goes preferentially into solution. Provided that the two components are distributed homogeneously, the respective solubility equilibrium is reached within approximately 0.5 hours.

It is known that the solubility equilibrium of hydrogenated isomaltulose suspensions in water is both concentration- and temperature-dependent. At constant temperature, the 1,6-GPS fraction in the solution increases with the amount of dry solid in the suspension. The solubility diagram of 1,1-GPM, 1,6-GPS and hydrogenated isomaltulose (see FIG. 4) shows that the solubility of the individual constituents increases continuously with increasing temperature. The process of the invention takes advantage of this observation.

1,000 kg of hydrogenated isomaltulose are dissolved in 265 kg water (process step 100, FIG. 1). The resulting suspension is heated for two hours at 85° C. (process step 200, FIG. 1), completely dissolving the hydrogenated isomaltulose. The educt concentration is then 77 wt. % solid phase content. The solution is subsequently crystallized by cooling, starting at a temperature of 85° C. until a temperature of 37° C. is reached. The cooling rate in the temperature range between 85° C. and 65° C. is 10 K/h; in the temperature range between 65° C. and 37° C., the cooling rate is adjusted to 1.2 K/h (process step 300).

The subsequent centrifugation step 400 produces large 1,1-GPM-rich crystals which can be separated readily from the 1,6-GPS-rich mother liquor. Centrifugation is carried out at 1,800 RPM for 0.5 hour or less. Advantageously, water, preferably 16 kg (1 kg per charge), can be added. The residue produced during centrifugation can be filtered for 1 to 2 hours at 6 bar, thereby separating additional crystallized solid. The 1,1-GPM fraction in the crystallized solid (561 kg crystallized solid) is 77.4 wt. % solid phase content, whereas the 1,6-GPS fraction in the crystallized solid is 22.1 wt. % solid phase content. The 1,1-GPM fraction in the mother liquor is 13.8 wt. % solid phase content, whereas the 1,6-GPS fraction in the mother liquor (560 kg mother liquor) is 84.0 wt. % solid phase content.

Example 2

Production of Pure 1,1-GPM

Figure 2:
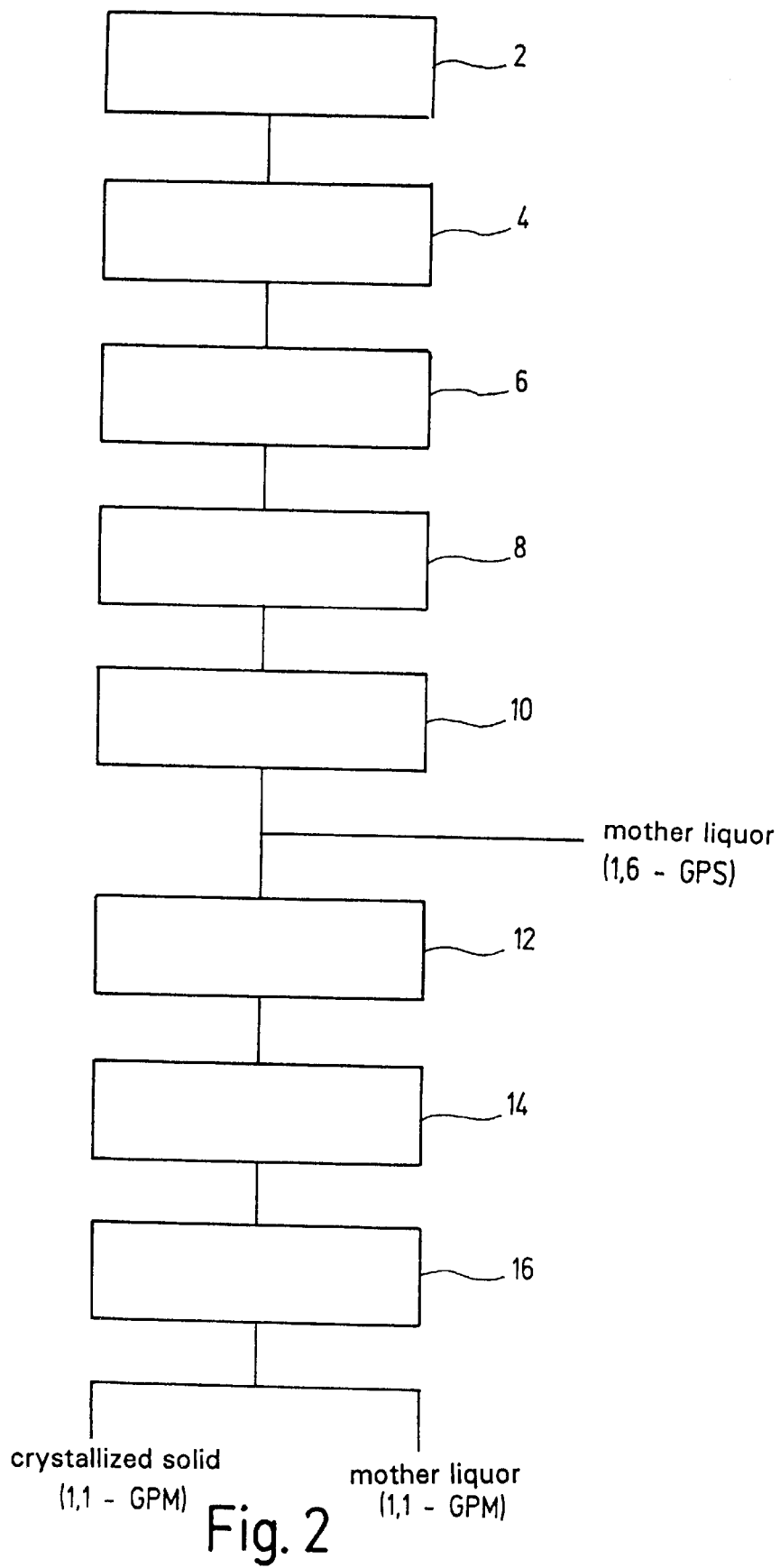
FIG. 2 is a schematic illustration of the process for producing pure 1,1-GPM.

Starting with the crystallized solid obtained in Example 1,which has a purity of 77 wt. % solid phase content, 561 kg of this crystallized solid were dissolved in 442 kg water (process step 2, FIG. 2). The temperature was adjusted to 60° C. The solution was filtered with a frame filter press to separate impurities (for example, impurities due to abrasion from apparatus seals) (process step 4, FIG. 2). The solution was subsequently concentrated in vacuum (0.02 bar) at 88° C. to yield 81 wt. % solid phase content (process step 6, FIG. 2). Thereafter, the solution was first crystallized by cooling between 88° C. and 37° C. (process step 8). A constant cooling rate of 9 K/h is maintained in the temperature range between 88° C. and 75° C. and a constant cooling rate of 1 K/h is maintained in the temperature range between 75° C. and 37° C. After centrifugation for 2 hours at 1800 RPM (process step 10), this first recrystallization increases the purity of the 1,1-GPM from 77 wt. % solid phase content to 95 wt. % solid phase content. The mother liquor produced during centrifugation is 1,6-GPS-rich.

The 1,1-GPM-rich crystallized solid (200 kg out of 334 kg which was produced as crystallized solid with 95 wt. % solid phase content) is dissolved in a small quantity of water at 95° C. (process step 12) and then again crystallized by cooling, in this case in the temperature range between 95° C. and 40° C. (process step 14, FIG. 2). The second recrystallization is carried out in a temperature range between 95° C. and 65° C. with a cooling rate of 3 K/h and in a temperature range between 65° C. and 40° C. with a cooling rate of 1 K/h. After centrifugation at 2900 RPM for two hours, 180 kg of a crystallized solid with 99 wt. % solid phase content of 1,1-GPM and a 1,1-GPM-rich mother liquor were obtained.

Without processing further the mother liquors, which still contained more 1,1-GPM, the process of the invention yielded in pure form more than 20 wt. % solid phase content of the 1,1-GPM contained in the hydrogenated isomaltulose.

Example 3

Production of Pure 1,6-GPS

Starting with the 1,6-GPS-rich mother liquor obtained in Example 1, which contained a 1,6-GPS-fraction with 84 wt.

Figure 3:
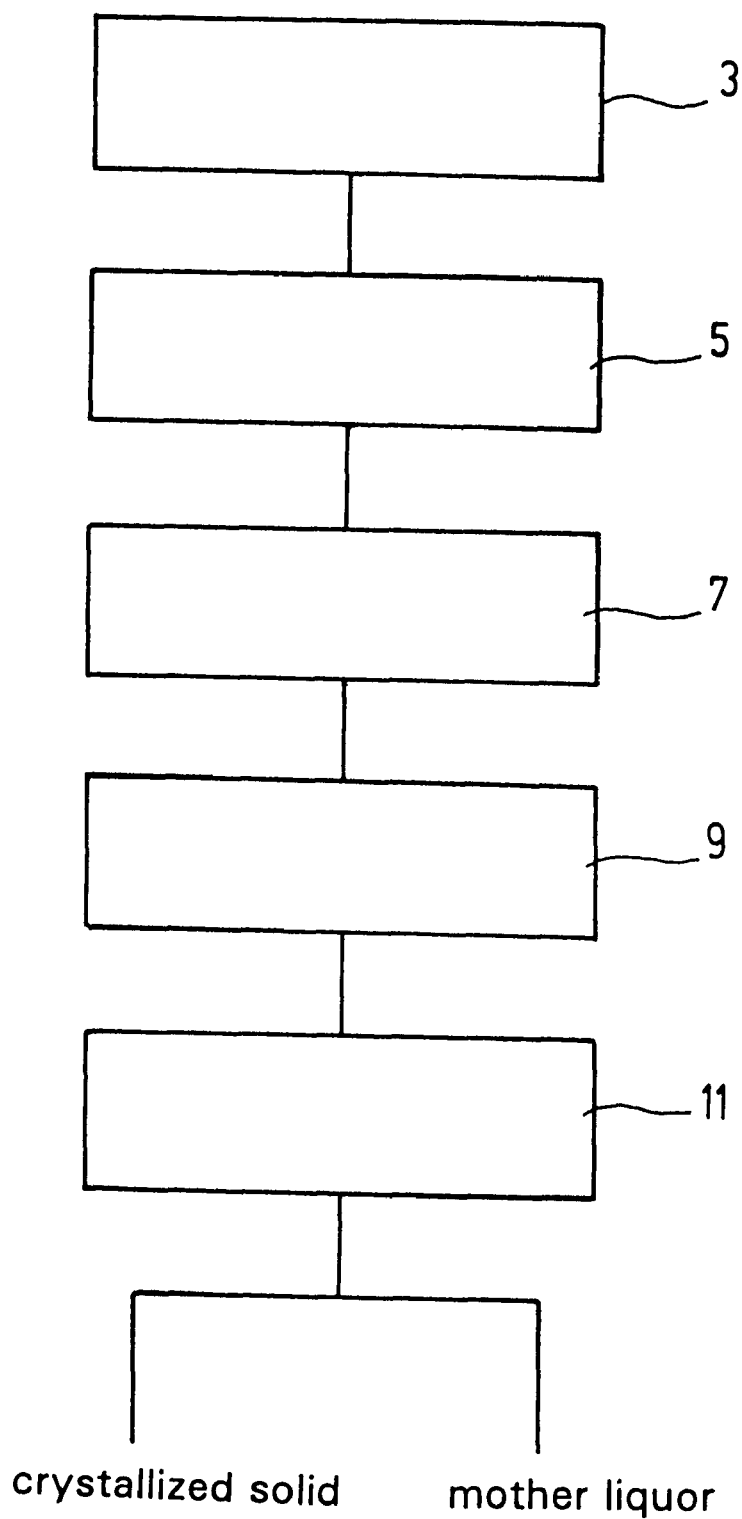
FIG. 3 is a schematic illustration of the process for producing pure 1,6-GPS.

% solid phase content, 560 kg of this mother liquor was initially concentrated at 55° C. (process step 3, FIG. 3). In this case, unlike the crystallization of 1,1-GPM, both the 1,6-GPS component, which is difficult to crystallize, and the 1,1-GPM component, which crystallizes readily, have to be crystallized.

In the process of the invention, the high 1,6-GPS content in the mother liquor is advantageously used to oversaturate the 1,6-GPS while keeping the fraction of solid phase content in the total solution low. While 1,6-GPS is being concentrated (process step 3, FIG. 3), the temperature of the solution should be maintained at or below 55° C. to prevent the 1,6-GPS crystals from melting. During the subsequent crystallization between 55° C. and 40° C. in cooling step 5 (process step 5, FIG. 3), the smallest feasible cooling rate should be maintained so as to produce preferably only 1,6-GPS nuclei. The cooling temperature should be kept as low as possible to prevent spontaneous crystallization of 1,1-GPM. According to the invention, the cooling rate in the temperature range between 55° C. and 40° C. is 0.3 K/h. The solution is then further concentrated at 55° C. (process step 7, FIG. 3). The solution is subsequently crystallized for a second time by cooling from 55° C. to 40° C. at a cooling rate of 0.3 K/h (process step 9, FIG. 3). The crystal mush produced after the second cool-down is centrifuged at 1800 RPM for 45 minutes (process step 11, FIG. 3). The crystallized solid (138 kg) is 1,6-GPS-rich with a 1,6-GPS contents of 99 wt. % solid phase content. The mother liquor produced by the centrifugation is also 1,6-GPS-rich.

As already mentioned in Example 2, the resulting mother liquors can be processed further to improve the process yield.

Example 4

Drying of the Pure 1,1-GPM and of the Pure 1,6-GPS

To improve the shelf life of 1,1-GPM and 1,6-GPS, the products described in the preceding examples are dried under vacuum in a temperature-controlled discontinuous tumble drier (contact drier). The rotating container of the tumble drier mixes dry and wet material continuously and thoroughly to achieve uniform drying. The vacuum of <0.02 bar removes not only the moisture, but also fine particles. These particles are separated by a cyclone filter.

1,6-GPS is dried for 5 hours at 45° C., thereby reducing the water content of 1,6-GPS from 2 to about 0.2 wt. %. Basically, no lumps are formed.

Unlike 1,6-GPS, 1,1-GPM occurs as a hydrated solid. The release of water from the solid at about 80° C. has to be taken into consideration when 1,1-GPM is dried, since the released water could dissolve the 1,1-GPM and cause the dried substance to cling together. The initial heating rate is therefore set to 1 K/h with a starting temperature of 35° C. The product is dry after 6 hours, containing only water of hydration; the water content is reduced from 9.4 to 9.3 wt. %. In this case, too, basically no lumps are formed.

Thus, while there have been shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Substitutions of elements from one described embodiment to another are also fully intended and contemplated. It is also to be understood that the drawings are not necessarily drawn to scale but that they are merely conceptual in nature. It is the intention, therefore, to be limited only as indicated by the scope of the claims appended hereto.

What is claimed is:

1. A process for crystallizing 1,1-GPM (1-0-α-D-Glucopyranosyl-D-mannite) and/or 1,6-GPS (6-0-α-D-Glucopyranosyl-D-sorbite), said process comprising:
    (i) dissolving hydrogenated isomaltulose or a mixture containing hydrogenated isomaltulose in water at an elevated temperature wherein said temperature is elevated such that said hydrogenated isomaltulose or mixture containing said hydrogenated isomaltulose is completely or almost completely dissolved in said water; and
    (ii) subjecting the dissolved solution produced in step (i) to one or more cooling steps within a temperature range of from about 90° C. to about 37° C. to produce distinct phases enriched in 1,1-GPM or 1,6-GPS, wherein said cooling step comprises
        (a) cooling from about 90° C. to about 65° C. at a rate of about 5 to about 15° C. per hour followed by
        (b) cooling from about 65° C. to about 37° C. at a rate of about 0.4 to about 3° C. per hour;
    wherein said cooling steps lead to phases of crystallization of 1,1-GPM and 1,6-GPS, wherein the crystalized solids obtained from the 1,1-GPM phase are coarse and uniform in grain size distribution so that said crystallized solids are easily separated, and wherein the process does not include seeding the solution.

2. A process for crystallizing 1,1-GPM (1-0-α-D-Glucopyranosyl-D-mannite) and/or 1,6-GPS (6-0-α-D-Glucopyranosyl-D-sorbite), said process comprising:
    (i) dissolving hydrogenated isomaltulose or a mixture containing hydrogenated isomaltulose in water at an elevated temperature wherein said temperature is elevated such that said hydrogenated isomaltulose or mixture containing said hydrogenated isomaltulose is completely or almost completely dissolved in said water; and
    (ii) subjecting the dissolved solution produced in step (i) to one or more cooling steps within a temperature range of from about 90° C. to about 37° C. to produce distinct phases enriched in 1,1-GPM or 1,6-GPS, wherein said cooling step comprises
        (a) cooling from about 90° C. to about 65° C. at a rate of about 5 to about 15° C. per hour followed by
        (b) cooling from about 65° C. to about 37° C. at a rate of about 0.4 to about 3° C. per hour, wherein the step further comprises seeding the solution with a seeding composition selected from the group consisting of hydrogenated isomaltulose, 1,1-GPM, and 1,6-GPS;
    wherein said cooling steps lead to phases of crystallization of 1,1-GPM and 1,6-GPS, and wherein the crystalized solids obtained from the 1,1-GPM phase are coarse and uniform in grain size distribution so that said crystallized solids are easily separated.

3. A process according to claim 1 or 2, wherein said cooling rate in step (a) is about 8 to about 12 K/h.

4. A process according to claim 1 or 2, wherein said cooling rate in step (b) is about 0.4 to 3 K/h.

5. A process according to claim 4 wherein said cooling rate in step (b) is about 0.8 to about 1.5 K/h.

6. A process according to claim 1 or 2, wherein said temperature range in step (ii) is from about 80–90° C. to about 30–40° C.

7. A process according to claim 6, wherein said temperature range in step (ii) is from about 85° C. to about 37° C.

8. A process according to claim 1 or 2, wherein the hydrogenated isomaltulose or a mixture containing hydrogenated isomaltulose is dissolved in water at an elevated temperature of about 80–90° C.

9. A process according to claim 8, wherein said elevated temperature is about 85° C.

10. A process according to claim 1 or 2, wherein the solution produced in step (i) has a concentration of hydrogenated isomaltulose or of a mixture containing hydrogenated isomaltulose of between about 70% and about 90% solid phase content by weight.

11. A process according to claim 10, wherein said concentration is between about 75% and about 85% solid phase content by weight.

12. A process according to claim 2, wherein said seeding composition comprises a suspension comprising hydrogenated isomaltulose in a solvent selected from the group consisting of water, isopropanol, and other suitable alcohols.

13. A process according to claim 12, wherein said solvent is water and isopropanol.

14. A process according to claim 13, wherein said suspension further comprises a food-compatible dispersing agent.

15. A process according to claim 2, wherein said seeding is carried out at a temperature between about 50° C. and about 65° C.

16. A process according to claim 15, wherein said seeding is carried out at a temperature between about 61° C. and about 63° C.

17. A process according to claim 1 or 2, wherein said separating is achieved by centrifugation.

18. A process according to claim 1 or 2, further comprising subjecting the phase enriched with, 1,1-GPM produced to one or more cooling steps, wherein said cooling step concentrates and/or crystallizes the 1,1-GPM present in said phase.

19. A process according to claim 18 further comprising purifying the 1,1-GPM-enriched phase prior to said cooling step.

20. A process according to claim 1 or 2, further comprising subjecting the phase enriched with 1,6-GPS produced to one or more cooling steps, wherein said cooling step concentrates and/or crystallizes the 1,6-GPS present in said phase.

21. A process according to claim 1 or 2, further comprising (iii) concentrating said enriched phases to about 60–90% solid phase content by weight, and (iv) obtaining a dry, crystalline product by evaporation.

22. A process according claim 18 further comprising drying the final 1,6-GPS for about 5 hours at about 45° C.

23. A process according claim 20 further comprising drying the final 1,1-GPM for about 6 hours from an initial temperature of about 35° C. using a heating rate of about 1 K/h.

24. A process according to claim 1 or 2, wherein the mixture containing hydrogenated isomaltulose comprises one or more of 1,1-GPM, 1,6-GPS, mannite, sorbite, 1,1-GPS (1-0-α-D-Glucopyranosyl-D-sorbite), isomelezitose, saccharose, or isomaltose.

* * * * *